United States Patent
Rocca et al.

(10) Patent No.: US 6,531,615 B2
(45) Date of Patent: Mar. 11, 2003

(54) PROCESS FOR THE OXIDATION OF CYCLOHEXANONE TO ε-CAPROLACTONE

(75) Inventors: Michael C. Rocca, Swinton (GB); Graham Carr, Liverpool (GB); Arnold B. Lambert, Heslington (GB); Duncan J. MacQuarrie, Middlethorpe Grove (GB); James H. Clark, Newland Park Close (GB)

(73) Assignee: Solvay (Societe Anonyme), Brussels (BE)

( * ) Notice: Subject to any disclaimer, the term of this patent is extended or adjusted under 35 U.S.C. 154(b) by 67 days.

(21) Appl. No.: 09/771,947

(22) Filed: Jan. 30, 2001

(65) Prior Publication Data

US 2001/0018399 A1 Aug. 30, 2001

(30) Foreign Application Priority Data

Jan. 31, 2000 (EP) .............................. 00300705

(51) Int. Cl.$^7$ ............................................ C07D 313/00
(52) U.S. Cl. ........................ 549/266; 502/246; 502/249; 502/224; 987/24; 568/771; 568/800; 568/803
(58) Field of Search ................... 502/224, 246, 502/249; 987/24; 568/771, 800, 803; 549/266

(56) References Cited

U.S. PATENT DOCUMENTS

| | | | | |
|---|---|---|---|---|
| 3,025,306 A | * | 3/1962 | Guest et al. | 260/343 |
| 4,353,832 A | * | 10/1982 | Lecloux et al. | 549/272 |
| 4,405,500 A | * | 9/1983 | Muller et al. | 252/433 |
| 4,740,603 A | * | 4/1988 | Lecoq et al. | 549/272 |
| 4,870,192 A | | 9/1989 | Chang et al. | |
| 4,994,583 A | * | 2/1991 | Pralus et al. | 549/272 |
| 5,288,841 A | * | 2/1994 | Bellis et al. | 528/275 |
| 5,712,213 A | | 1/1998 | Joly et al. | |
| 5,883,156 A | * | 3/1999 | Fukuda et al. | 523/122 |
| 6,156,910 A | * | 12/2000 | Ueno | 549/266 |

FOREIGN PATENT DOCUMENTS

GB  1070322  6/1967

OTHER PUBLICATIONS

Organic Reactions; "The Baeyer×Villiger Oxidation of Aldehydes and Ketones", C.H. Hassall, 1957, 9, 73. Month N/A.
Organic Reactions, "The Baeyer–Villger Oxidation of Ketones and Aldehydes", G.R. Krow; 1993, vol. 43, 251. Month N/A.
Journal of the American Chemical Society; "Biphase and Triphase Catalysis, Arsonated Polystyrenes as Catalysis, ..." 101:23/Nov. 7, 1979; Jacobson et al.
Organometallics, vol. 13, 3442–33451; "Platinum–Catalyzed Oxidations with Hydrogen Peroxide: ..." Gusso et al. Dec. 1993.
Chemistry Letters, "The Synthesis of Solid Super Acids and the Activity for the Reactions of ..."; Tanabe et al.; pp. 625–626, 1976. Month N/A.
Science, "A Neutral Templating Route to Mesoporous Molecular Sieves", vol. 267, Feb. 10, 1995; Tanev et al.
J. Chem. Soc. Faraday Trans.; "Antimoney(V) Oxide Grafted onto a Silica Gel Surface: Acidic ...", 1992, 88(21), 3193–3196. Month N/A.

* cited by examiner

Primary Examiner—Mark L. Bell
Assistant Examiner—Patricia L. Hailey
(74) Attorney, Agent, or Firm—Larson & Taylor PLC

(57) ABSTRACT

This invention relates to a composition comprising antimony trifluoride and silica, a method for the preparation of said composition and use of said composition as a catalyst in a process for the oxidation of cyclohexanone to ε-caprolactone.

8 Claims, 2 Drawing Sheets

PROCESS FOR THE OXIDATION OF CYCLOHEXANONE TO ε-CAPROLACTONE

This invention relates to a composition comprising antimony trifluoride and silica, a method for the preparation of said composition and certain uses of said composition, in particular its use as catalyst.

The Baeyer-Villiger oxidation of ketones to lactones or esters (A. Baeyer and V. Villiger, Ber., 1899, vol. 32, page 3625) is a widely used synthetic method and has been comprehensively reviewed (C. H. Hassall, Org. React., 1957, vol. 9, page 73; G. R. Krow, Org. React., 1993, vol. 42, page 251). An example is the oxidation of cyclohexanone to ε-caprolactone, which is of particular industrial interest since it is extensively used in the synthesis of polycaprolactones.

The most common reagents used for the Baeyer-Villiger oxidation of ketones to lactones or esters are peroxycarboxylic acids (e.g. peracetic acid, m-chloroperbenzoic acid). These are commercially available on a large scale, but their industrial use is impractical for safety and cost reasons. In particular, they are shock sensitive in their pure form and may be explosive in the condensed phase. Moreover, they yield the corresponding carboxylic acid products, which may give rise to separation and recycling problems.

In order to avoid the use of these potentially dangerous materials and to lower the environmental impact of the waste produced, various other oxidation systems using hydrogen peroxide as the oxidant have been developed. (J. D. McClure et al., J. Org. Chem., 1962, vol 27,24; S E. Jacobsen et al., J. Am. Chem. Soc., 1979, vol. 101,6938; A. Gusso et al., Organometallics, 1994, vol. 13, 3442). For example, the following compounds have been used in conjunction with hydrogen peroxide—boron trifluoride etherate, borax ($Na_2B_4O_7$), arsenic containing compounds, cationic platinum complexes, molybdenum complexes, methyltrioxorhenium, selenium compounds, titanium silicate, zeolites, sulfonated resins and sodium hydroxide.

Tanabe and Hattori have made solid superacids based on antimony pentafluoride supported on silica and other metal oxides (K. Tanabe et al., Chem. Lett., 1976, 625), but antimony trifluoride supported on silica has not been reported or even suggested, and neither has its use as catalyst in Baeyer-Villiger oxidations.

Accordingly, the present invention provides a composition comprising antimony trifluoride and silica. As used herein, "silica" is defined as any form of a dioxide of silicon. Forms of silica may be hydrated. Forms of silica include a crystalline quartz form; a crystalline cristobalite form; a crystalline tridymite form; a crytocrystalline chalcedony form; an amorphous form; an amorphous opal form; an amorphous granular hydrated form (silica-gel); a form including aluminium atoms, such as an aluminosilicate; and a mesoporous form, such as HMS hexagonal mesoporous silica. Preferably the silica comprises HMS or silica-gel; more preferably the silica comprises HMS.

Preferably the composition is substantially pure. If present, materials other than antimony trifluoride and silica are preferably present in only trace amounts. Preferably the antimony trifluoride is present in an amount of up to about 2 mmol $SbF_3$ per gram of composition, more preferably the antimony trifluoride is present in an amount of between 0.1 and 1.5 mmol, preferably 0.5 to 1.5 mmol $SbF_3$ per gram of composition. Amounts of 1 to 2 mmol $SbF_3$ per gram of composition can lead to good results.

Preferably, the composition is in the form of a powder having a mean particle size, specific surface area (SA) and average pore diameter (APD) which depend on those of the starting silica. Generally, the SA is below or equal to 1300 $m^2/g$, in particular 1250 $m^2/g$, or even below or equal to 1000 $m^2/g$ in the case of HMS, and below or equal to 600 $m^2g$, in particular 530 $m^2/g$, or even below or equal to 450 $m^2/g$ in the case of silica-gel. The SA is generally above 300 $m^2/g$, and even above 700 $m^2/g$ in the case of HMS. And typically, the APD is below or equal to 10 nm, in particular 6 nm. The APD is generally above 1 nm, in particular 2 nm. The APD is mostly close to or superior to 3 nm in the case of HMS, and it may be close to 6 nm in the case of silica-gel.

The present invention further comprises a process comprising the use of the composition comprising antimony trifluoride and silica as a catalyst. Reactions may be carried out as a batch process or in a continuous process. Preferably the composition catalyses an organic oxidation reaction. Preferably hydrogen peroxide is used as oxidising agent. Preferably the composition calalyses an oxidation of a ketone to a lactone or ester, more preferably the composition catalyses the oxidation of cyclohexanone to ε-caprolactone.

It may also catalyse the oxidation of cyclopentanone to valerolactone and the oxidation of cycloheptanone to enantholactone.

The oxidation of cyclohexanone to ε-caprolactone may be carried out as a batch process or a continuous process. In a batch process, the composition, cyclohexanone and hydrogen peroxide are mixed and allowed to react. In a continuous process, cyclohexanone and hydrogen peroxide may, for example, be passed through a column containing the composition. The product may be removed from the reaction mixture in subsequent separation steps.

Preferably the process of the oxidation of cyclohexanone to ε-caprolactone comprises the steps of:
a) mixing the composition with cyclohexanone,
b) adding hydrogen peroxide to the mixture, and
c) allowing the reaction to proceed.

These steps can be carried out successively, in a batch process, or simultaneously in a continuous process.

Typically, step (a) is performed at a temperature of up to about 70° C. More preferably, step (a) is performed at room temperature. Typically step (b) is performed over a period of between about 5 minutes to about 120 minutes preferably over about 30 minutes. Typically in steps (b) and (c) the reaction is maintained at a temperature of up to about 110° C., preferably at a temperature of between about 60° C. and about 100° C., more preferably between about 70° C. and 90° C. It has been found that raising the temperature can improve yields but is detrimental to the recovery of the catalyst. Typically step (c) is performed at a pressure at which the reaction mixture boils (in order to remove water azeotropically). Preferably step (c) is performed at a pressure of between 50 and 150 mbar. Preferably steps (a), (b) and (c) is performed under stirring.

Preferably a molar excess of cyclohexanone is used relative to hydrogen peroxide. Preferably the molar ratio of cyclohexanone: hydrogen peroxide is up to about 5:1, more preferably from about 2:1 to about 3:1, more preferably about 2.5:1. Preferably the composition is used in an amount of up to 10 g per 100 ml of cylcohexanone, more preferably the composition is used in an amount of up to 5 g per 100 ml of cyclohexanone, even more preferably the composition is used in an amount of up to 2 g per 100 ml of cyclohexnone.

Preferably water is constantly removed from the reaction mixture. This gives the advantage of limiting the formation of unwanted by-products which can be formed through the ring opening of the lactone under the action of water. Any suitable means may be used for removing water, for example azeotropic removal or use of a dessicant. Preferably the water is removed azeotropically.

Preferably hydrogen peroxide is a 30% to 90% solution in water, more preferably hydrogen peroxide is a 70 to 85% solution in water, for instance an about 85% solution in water. However, a 65–75%, and especially a 70% H2O2 solution was surprisingly more effective than a 80–90%, and especially a 86% H2O2 solution, which shows that the presence of a small amount of water during the reaction may be beneficial.

Alternative oxidising agents include agents capable of generating hydrogen peroxide in situ and other peroxides such as sodium percarbonate and sodium perborate.

The present invention further provides a method for the preparation of the composition comprising antimony trifluoride and silica, comprising the step of treating silica with antimony trifluoride. Preferably the silica is selected from the group consisting of HMS and silica-gel.

Preferably the method comprises the steps of:
a) synthesising HMS using a template,
b) removing the template either by calcination to yield a calcinate HMS support (herein exemplified as HMS-C) or by solvent extraction and subsequent drying to yield a dried HMS support (herein exemplified as HMS-E), and
c) treating the calcinated HMS with antimony trifluoride to yield a composition of the present invention or theating the dried HMS with antimony trifluoride to yield a composition of the present invention.

Alternatively the method comprises the steps of:
a) calcinating silica-gel to yield a calcinated silica-gel support (herein exemplified as K-600), or drying silica-gel to yield a dried silica-gel support (herein exemplified as K-120), and
b) treating the calcinated silica-gel with antimony trifluoride to yield a composition of the present invention or treating the dried silica-gel with antimony trifluoride to yield a composition of the present invention.

Preferably the calcination of the silica is performed at a temperature in the rang of about 250° C. to about 650° C. Preferably the drying of the silica is performed at a temperature in the range of about 100° C. to about 250° C.

Preferably the step of treating the silica with antimony trifluoride comprises the step of treating the silica with a refluxing mixture of antimony trifluoride in toluene. The handling (exposure to air) of SbF3 should be avoided prior to this treatment step.

Figure 1:
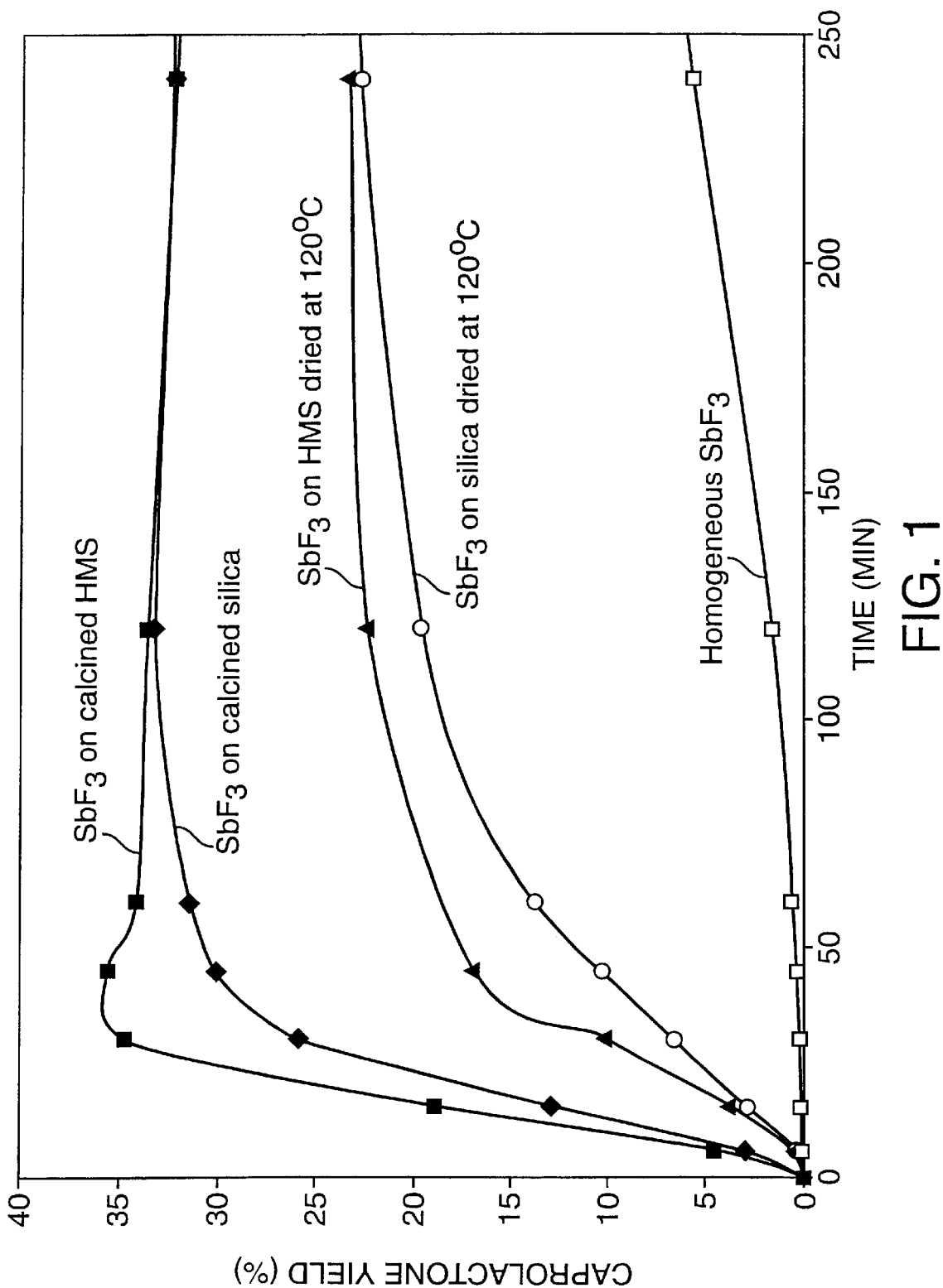
FIG. 1 is a graph showing the rates of formation of ε-caprolactone from cyclohexanone using various antimony trifluoride catalysts.

The present invention shall now be described by way of examples in order to illustrate the invention without however limiting its scope.

HMS support was synthesised according to the method described by Tanev and Pinnavaia (Science, 1995, vol 267, 865), using 1-aminododecane as a template, which was removed either by calcination of the material for 7 hours in air at 600° C. leading to support HMS-C, or by ethanol extraction leading to HMS-E support. Immediately after calcination (avoiding rehydration), the material was treated with a refluxing mixture of antimony trifluoride (for example 1 mmol SbF$_3$ per gram of HMS-C) in sodium dried toluene for 20 hours followed by solvent evaporation on a rotary evaporator. The resulting white fine flowing powder (HMS-C-SbF$_3$) can be handled and stored in air without loss of catalytic activity. In the case where the template was removed by ethanol extraction, the HMS was dried at 120° C. in a vacuum oven for 4 hours prior to treatment with refluxing antimony trifluoride in sodium dried toluene (HMS-E-SbF$_3$). Commercial silica (Merck, Kieselgel 60) was also used as a support after drying at 120° C. (K-120-SbF$_3$) or at 600° C. (K-600-SbF$_3$).

The DRIFT (Diffuse Reflectance Infra Red Fourier Transform spectroscopy) spectra of the various catalysts prepared showed no apparent difference to those of underivatised HMS or Kieselgel. Simultaneous Thermal Analysis (STA) traces of various batches of the catalyst, when compared with pure SbF$_3$, suggest that antimony trifluoride reacted with the silica surface to yield as yet undetermined surface species. A $^{19}$F CP-MAS-NMR was performed on a HMS-E-SbF$_3$ with CFCl$_3$ as internal standard. The broad peak at −63.8 ppm observed in the composition but is replaced by two peaks at −122.2 ppm (sharp) an −154 ppm (broad), indicating that SbF$_3$ and silica have reacted. The acidic character of the surface of the catalysts was probed via pyridine absorption, which showed that the catalysts possess both Lewis acid sites (IR band at 1489 cm$^{-1}$, possibly due to coordinatively unsaturated antimony centres) and Bronsted acid sites (1540 cm$^{-1}$, possibly due to the polarisation of surface hydroxyl groups by antimony trifluoride) (see E. V. Benvenutti et al., J. Chem. Soc. Faraday Trans., 1992, vol 88(21), 3193–3196). In an aqueous environment, the Lewis acid sites can bind water molecules, which will exhibit Bronsted acidity. By potentiometrically titrating aqueous suspensions of the catalysts with sodium hydroxide, the number of acid sites in the catalysts could be determined (Table 1).

TABLE 1

Number of acid sites on the supported SbF$_3$ catalysts measured by titration.

| Material | Loading (mmol SbF$_3$ per gram of composition) | Total number of acid sites | Number of acid sites per SbF$_3$ molecule |
|---|---|---|---|
| K-600-SbF$_3$ | 1 | 1.63 | 1.63 |
| HMS-C-SbF$_3$ | 0.5 | 1.5 | 3 |
| HMS-C-SbF$_3$ | 1 | 1.94 | 1.94 |
| HMS-C-SbF$_3$ | 2 | 3.3 | 1.65 |
| HMS-E-SbF$_3$ | 1 | 2.1 | 2.1 |

At the same loading of antimony trifluoride, fewer acid sites are formed on the calcined silica-gel support than on calcined HMS support. The drying temperature of HMS supports does not seem to significantly influence the concentration of acid sites generated, but the SbF$_3$ loading does. At a loading of 0.5 mmol SbF$_3$ per gram of composition, three acid sites are generated per SbF$_3$ molecule, while at 1 mmol SbF$_3$ per gram of composition, only two acid sites per SbF$_3$ molecule, and at 2 mmol SbF$_3$ per gram of composition only ca. 1.5 acid site per SbF$_3$ molecule are generated. Without limitation to the scope of the present invention, an explanation for this could be that antimony trifluoride reacts with the silanols to form some surface species (F$_2$Sb—O), which by polarisation of surrounding hydroxyls give rise to several Bronsted acid centres. Increasing the amount of antimony trifluoride decreases the amount of available hydroxyls and hence the number of acid sites.

The nitrogen adsorption isotherms of the various HMS supported catalysts are consistent with the structure of HMS materials. All the prepared catalysts show a lower surface area than that of the starting material (Table 2), which is understandable since the smallest pores may be blocked by antimony trifluoride. The average pore diameter should therefore be larger than that of the parent material, which is the case when the support was pre-treated at 120° C., but not when it was calcined.

TABLE 2

Surface areas and average pore size diameters of the supported $SbF_3$ catalysts.

| Material | Loading (mmol $SbF_3$ per gram of composition) | BET Surface Area (m²/g) | Average Pore Diameter (nm) |
|---|---|---|---|
| Kieselgel 60 | — | 529 | 5.7 |
| K-120-$SbF_3$ | 1 | 383.5 | 5.9 |
| K-600-$SbF_3$ | 1 | 395 | 5.7 |
| Calcined HMS | — | 1151 | 3.05 |
| HMS-C-$SbF_3$ | 0.5 | 835 | 3 |
| HMS-C-$SbF_3$ | 1 | 843 | 2.98 |
| HMS-C-$SbF_3$ | 2 | 712 | 2.95 |
| EtOH extracted HMS | — | 1254 | 3.7 |
| HMS-E-$SbF_3$ | 1 | 998 | 4.1 |

The catalysts show a high efficiency in catalysing the oxidation of cyclohexanone to ε-caprolactone. Excess cyclohexanone (25 ml) was used to allow continuous azeotropic removal of the water under reduced pressure (~80 mbar/70° C.). The catalyst (0.5 g) was mixed with cyclohexanone and heated up to 70° C. before hydrogen peroxide (70%, 4.7 g) was added dropwise over 30 minutes, using a peristaltic pump. $^1$H NMR was used to monitor the reaction because of the formation of stable cyclohexanone peroxides, which decompose in GC injectors to give caprolactone, cyclohexanone and other products.

Control reactions with no catalyst and with underivatised HMS were also carried out. Under those conditions, cyclohexanone oxidation did not occur to more than 2% (based on the amount of hydrogen peroxide introduced) after six hours. Antimony trifluoride without silica support did catalyse the reaction, but the kinetics of the oxidation was much slower than with supported antimony trifluoride (FIG. 1). At equivalent $SbF_3$ loading and support pre-treatment, HMS supported catalysts are more efficient than their Kieselgel analogues (FIG. 1), possibly because of their higher surface area.

Re-use experiments showed that the catalyst does not lose activity, but actually gets slightly more active from one run to the other, increasing the caprolactone yield from 27% to 33% between the first and third use of HMS-E-$SbF_3$. The effect of drying the support prior to reacting antimony trifluoride with its surface is very important for the catalytic properties of the resulting material. With $SbF_3$ supported on calcined HMS, which has not been allowed to rehydrate, better yields of caprolactone can be obtained than with $SbF_3$ supported on HMS dried at 120° C. Both the water content of the support and the nature of its surface before $SbF_3$ grafting are important to the final catalytic properties, possibly because the calcined HMS surface mainly presents siloxane bridges, as opposed to silanols for the HMS dried at 120° C.

When HMS-C-$SbF_3$ is used, caprolactone production stops about 15 minutes after the addition of hydrogen peroxide is stopped, and then the caprolactone is gradually converted to hydroxy-caproic acid and low molecular weight polycaprolactone. The analysis of the reaction mixture at 60 minutes shows that its active oxygen content is less than 1%, indicating that most of the hydrogen peroxide has reacted.

Figure 2:
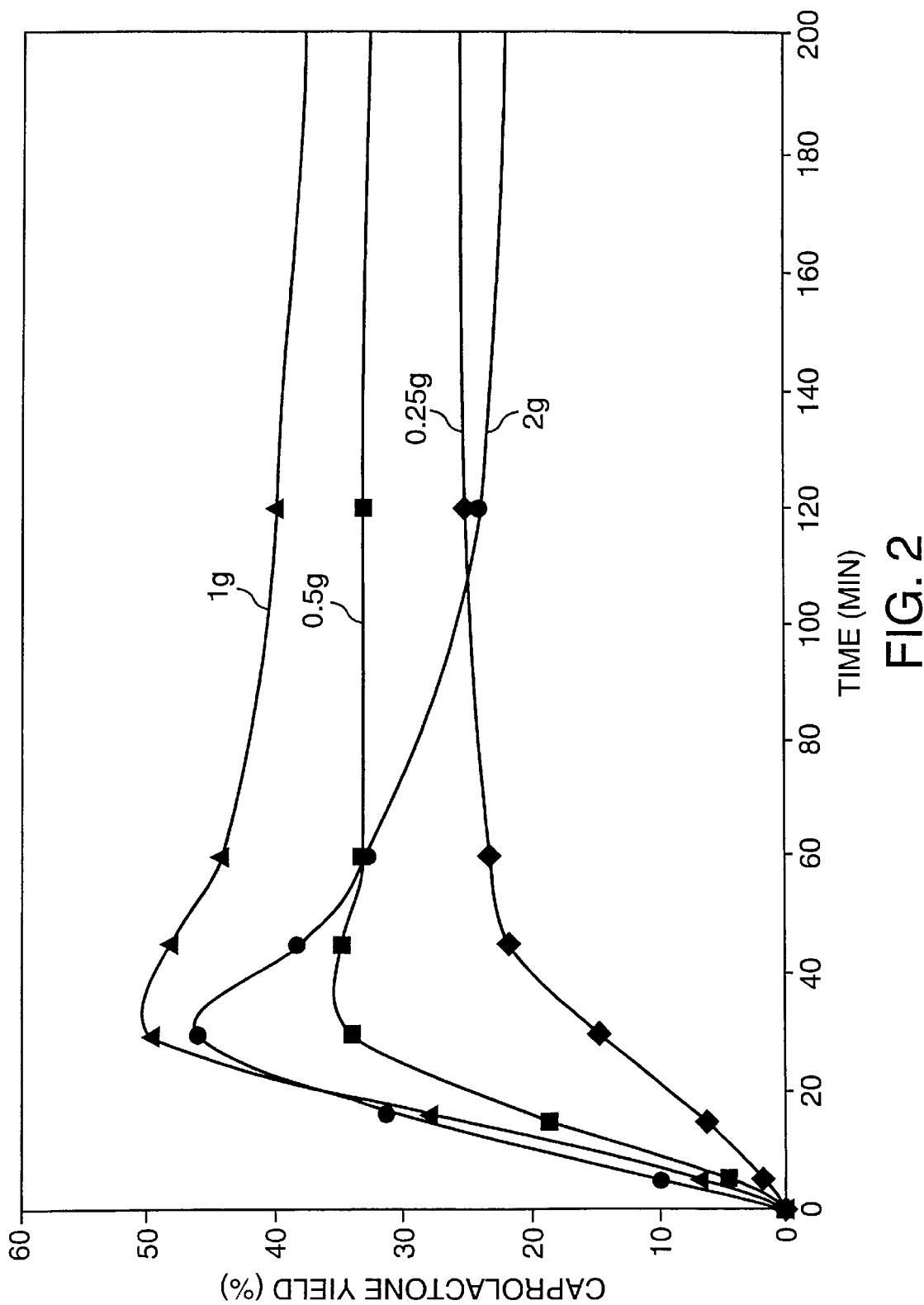
FIG. 2 is a graph showing the effect of increasing quantity of the HMS-C-SbF$_3$ catalyst on the conversion of cyclohexanone to ε-caprolactone.

Variation of the quantity of catalyst (HMS-C-$SbF_3$) at 70° C. showed that the reaction rate is dependent on the amount of catalyst used, but that the quantity of polycaprolactone and hydroxy-caproic acid produced is even more influenced by this factor. Hence, larger quantities of catalyst lead to poor caprolactone yield and high yields of hydroxy-caproic acid polycaprolactone (FIG. 2).

The effect of the $SbF_3$ loading on the activity of the HMS-C-$SbF_3$ catalyst has also been investigated. When it is increased to 2 mmol $SbF_3$ per gram of composition, the initial rate of the reaction is faster and the best caprolactone yield obtained at 70° C. is 40.3% (34.6 with a loading of 1 mmol $SbF_3$ per gram of composition, but the amount of by-products is also increased. On the other hand, with a lower loading of 0.5 mmol $SbF_3$ per gram of composition, even though the initial rate of reaction is slightly slower, the yield of caprolactone after 45 minutes is comparable to that obtained with a 1 mmol $SbF_3$ per gram of composition catalyst, and the by-products formation is halved.

When the reaction is run at 90° C. (130 mbar), the efficiency of the catalysts is even greater, enabling yields of ca. 70% of caprolactone to be obtained in 45 minutes. At this temperature, 1 and 2 mmol $SbF_3$ per gram of catalysts based on calcined HMS show the same activity and give comparable amounts of by-products. But when the amount of catalyst used is increased, so is the amount of by-products formed.

What is claimed is:

1. A process for the oxidation of cyclohexanone to ε-caprolactone comprising:

reacting cyclohexanone with hydrogen peroxide in the presence of a catalyst comprising antimony trifluoride and hexagonal mesoporous silica.

2. The process of claim 1, wherein said reacting comprises the steps of:

a) mixing the catalyst with cyclohexanone to form a mixture b) adding hydrogen peroxide to the mixture, and c) allowing the reaction to proceed.

3. The process of claim 2, wherein step (a) is performed at a temperature of up to about 70° C. and step (b) is performed over a period of between about 5 minutes and about 120 minutes.

4. The process of claim 2, wherein in steps (b) and (c) the reaction is maintained at a temperature of between about 60° C. and 100° C.

5. The process of claim 2, wherein step (c) is performed at a pressure of between 50 and 150 mbar.

6. The process of claim 1, wherein the molar ratio of cyclohexanone to hydrogen peroxide is from about 2:1 about 3:1.

7. The process of claim 1, wherein the catalyst is used in an amount of up to 2 g per 100 ml of cyclohexanone.

8. The process of claim 1, wherein catalyst in an amount of between 0.1 and 1.5 mmol $SbF_3$ per gram of catalyst.

* * * * *